United States Patent [19]

Helixon et al.

[11] 4,091,812
[45] May 30, 1978

[54] OPERATOR MEANS FOR SYRINGE CARTRIDGES

[75] Inventors: Michael L. Helixon; Barry S. Ward, both of Fort Worth, Tex.

[73] Assignee: Alcon Laboratories, Inc., Fort Worth, Tex.

[21] Appl. No.: 650,248

[22] Filed: Jan. 19, 1976

[51] Int. Cl.² ............................................. A61M 5/00
[52] U.S. Cl. ............................ 128/218 D; 128/218 PA
[58] Field of Search ............ 128/218 R, 218 P, 218 D, 128/218 DA, 218 S, 220, 221, 234, 215

[56] References Cited

U.S. PATENT DOCUMENTS

| 2,453,590 | 11/1948 | Poux | 128/218 D |
|---|---|---|---|
| 2,490,553 | 12/1949 | Smith | 128/220 |
| 2,574,339 | 11/1951 | Lockhart | 128/220 |
| 2,646,798 | 7/1953 | Brown | 128/218 D |
| 2,688,965 | 9/1954 | Huber | 128/218 D |
| 2,859,750 | 11/1958 | Stroop | 128/218 D |
| 2,860,635 | 11/1958 | Wilburn | 128/218 S |
| 3,115,135 | 12/1963 | Sarnoff | 128/218 DA |

Primary Examiner—John D. Yasko
Attorney, Agent, or Firm—Fitch, Even, Tabin & Luedeka

[57] ABSTRACT

A syringe device is disclosed which employs an operator cooperable with the plunger of a syringe cartridge to facilitate discharge of fluid from the syringe cartridge. Various embodiments of the operator each include a sleeve portion which progressively telescopes the barrel of the syringe cartridge to prevent its fracture and lend stability to the assembly during operation. The operators are cooperable with the syringe cartridge to selectively discharge one or more predetermined dosages from the syringe.

5 Claims, 10 Drawing Figures

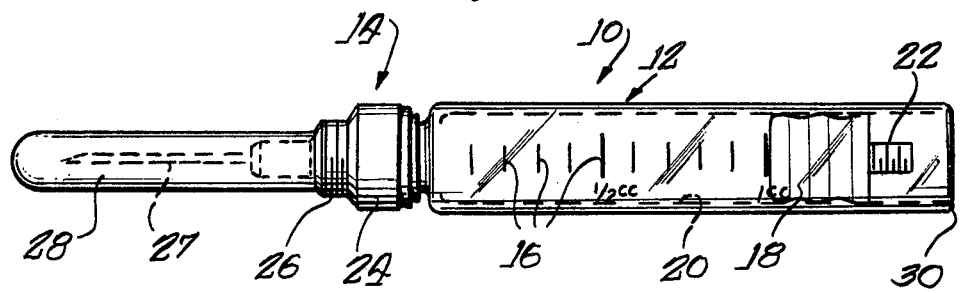
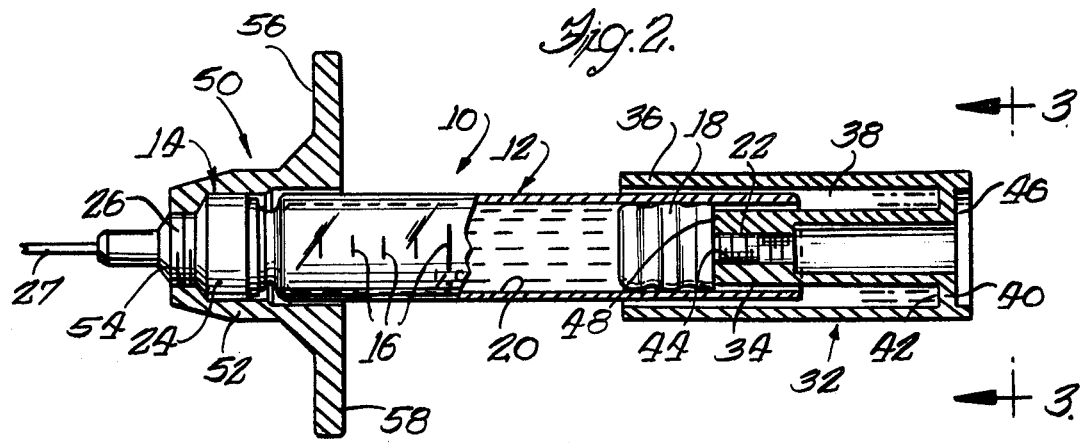
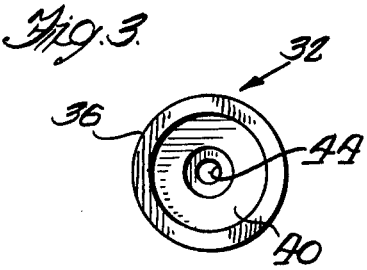
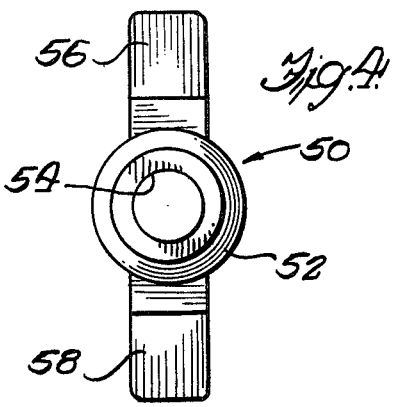
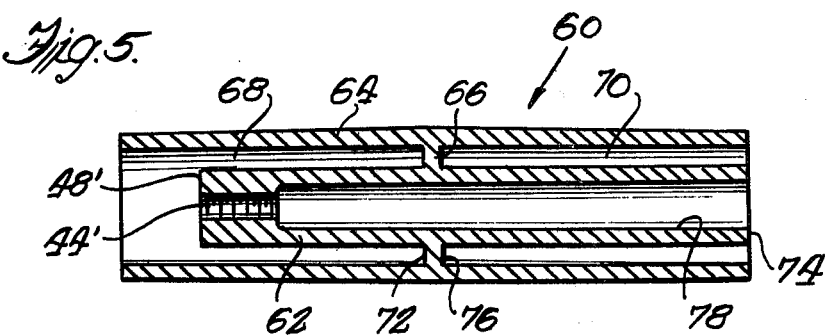

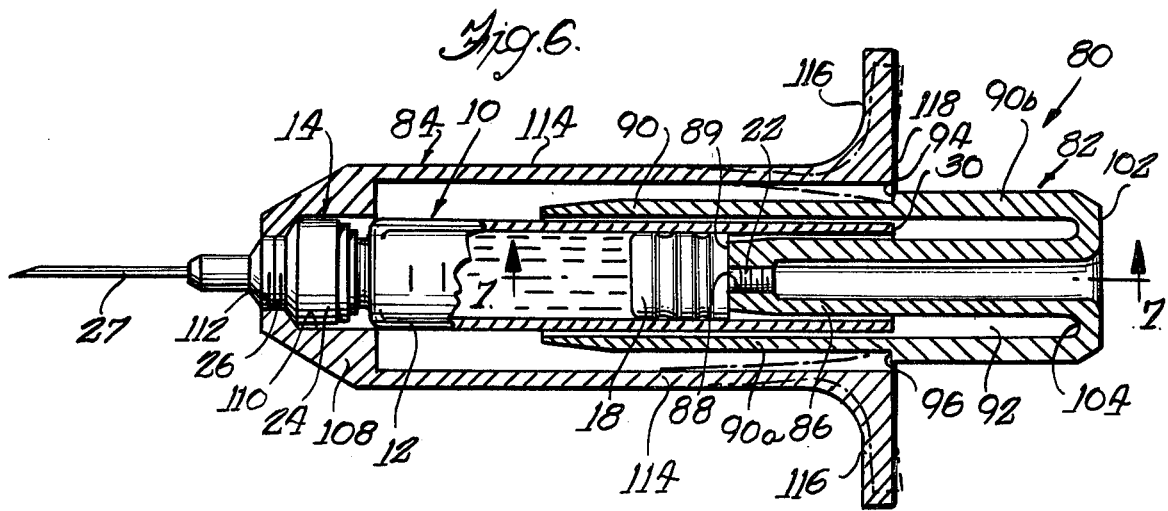
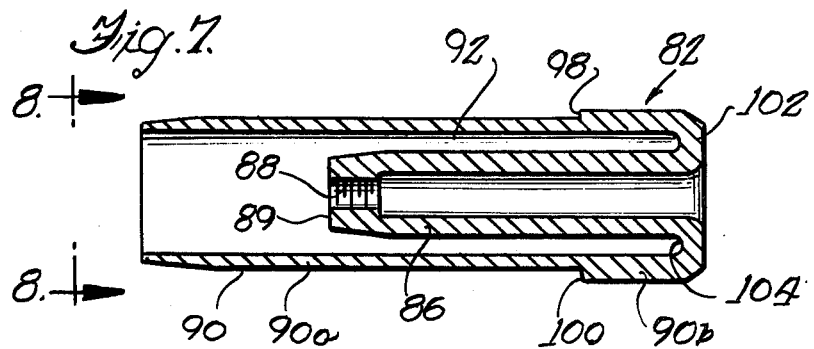
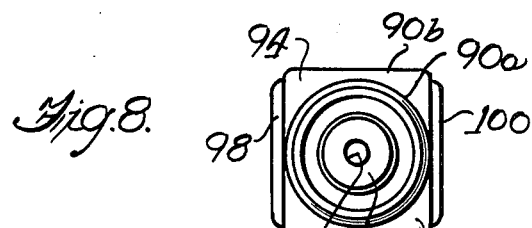
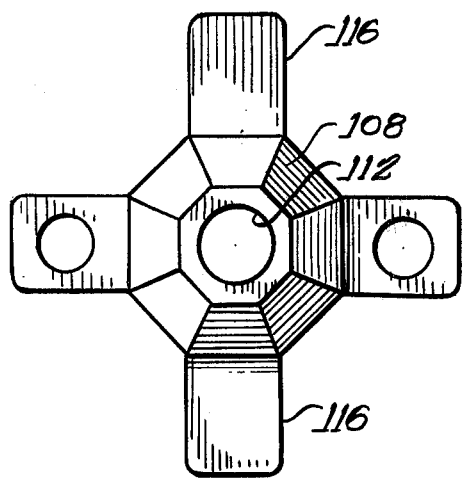
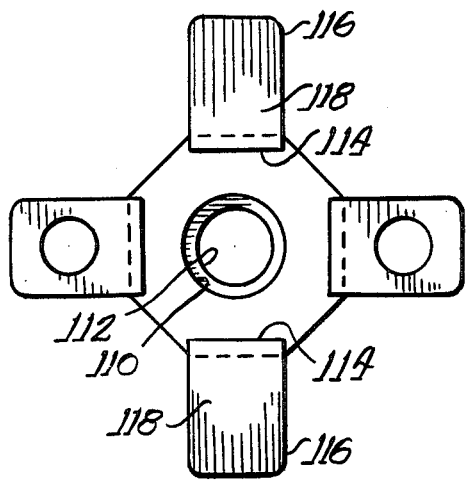

OPERATOR MEANS FOR SYRINGE CARTRIDGES

The present invention relates generally to syringe devices, and more particularly to novel operator means for use with disposable syringe cartridges to facilitate discharge of one or more predetermined dosages from a cartridge while protecting the syringe barrel from fracture during operation.

Syringe devices are generally known which include means for limiting the dosage that can be discharged from the syringe. Syringe devices having means to effect predetermined dosage discharge during operation are particularly important in applications of home use where the person using the syringe for injection into himself or another person is relatively untrained in the art of dosage control. Conventionally, in contemporary syringe devices provided for either home or institutional use, a syringe cartridge is employed which is often disposable and includes a barrel made of a breakable plastic or glass. The syringe cartridge is at least partially "prefilled" with a particular medicinal fluid and is adapted to have a discharge needle secured thereon such that a plunger within the barrel may be moved longitudinally in a manner to effect discharge through the needle. The syringe cartridge is generally inserted into a fixture adapted for hand manipulation to move the plunger and effect the desired discharge.

The present invention is directed to operator means for use with such a syringe cartridge to allow easy and exacting manipulation in discharging one or more predetermined dosages from the syringe cartridge. The operator means in accordance with the present invention further provide for protecting the syringe cartridge barrel during use so as to prevent breakage of the barrel.

Accordingly, one of the primary objects of the present invention is to provide novel operator means for use with a syringe cartridge and the like to effect predetermined dosage discharge from the syringe.

Another object of the present invention is to provide operator means for use with a syringe device wherein a single operator may be manipulated to effect discharge of different predetermined dosages from the syringe cartridge.

Yet another object of the present invention is to provide operator means for use with a syringe cartridge wherein the operator means includes a protective sleeve which progressively telescopes the syringe barrel during use to stabilize the operator means and prevent fracture of the cartridge barrel.

Still another object of the present invention is to provide, in combination, a syringe cartridge having novel cartridge holder means cooperable with an operator to effect selective discharge of predetermined dosages from the syringe cartridge.

Further objects and advantages of the present invention, together with the organization and manner of operation thereof, will become apparent from the following detailed description of the invention when taken in conjunction with the accompanying drawings, wherein:

FIG. 1 is a side elevational view of a syringe cartridge of the type with which the present invention finds particular application;

FIG. 2 is a longitudinal sectional view showing the syringe cartridge of FIG. 1 having operator means operatively associated therewith in accordance with the present invention;

FIG. 3 is an end view of the operator member of FIG. 2, taken substantially along the line 3—3 of FIG. 2 and looking in the direction of the arrows;

FIG. 4 is a front elevational view of the syringe cartridge holder employed in the embodiment of FIG. 2;

FIG. 5 is a longitudinal sectional view of another embodiment of an operator in accordance with the present invention for use with the syringe cartridge of FIG. 1 to effect discharge of two predetermined dosages from the syringe cartridge;

FIG. 6 is a longitudinal sectional view, partly in elevation, similar to FIG. 2 but showing the syringe cartridge in cooperation with an operator and syringe holder in accordance with another embodiment of the present invention which is adapted to effect selective discharge of three predetermined dosages from the syringe cartridge;

FIG. 7 is a longitudinal sectional view of the operator shown in FIG. 4 but rotated 90° about its longitudinal axis;

FIG. 8 is an end view of the operator of FIG. 7, taken substantially along the line 8—8 of FIG. 7 and looking in the direction of the arrows;

FIG. 9 is a rear end view of the holder shown in FIG. 6; and

FIG. 10 is a front end view of the holder shown in FIG. 6.

Referring now to the drawings, and in particular to FIG. 1, a syringe cartridge is indicated generally at 10. The syringe cartridge 10 may be disposable after a single usage and is of the type with which the present invention, to be described more fully hereinafter, finds particular application. The syringe cartridge 10 is of generally known design and includes a cylindrical tubular barrel, indicated generally at 12, and a discharge end, indicated generally at 14. Conventionally, the barrel portion 12 is made of glass or other suitable, preferably transparent, relatively thin walled material and bears indicia, such as indicated at 16, along the longitudinal length of the outer surface of the barrel to indicate the volume of fluid within the barrel. The syringe cartridge 10 is adapted to contain a predetermined quantity of fluid, such as a medicinal fluid, which is retained within the chamber defined within the barrel 12 by a plunger 18. The plunger 18 is conventionally made of a material such as rubber having an outer cylindrical surface sufficient to sealingly and slidingly engage an interior surface 20 of the tubular barrel 12. The plunger 18 has a threaded connector shaft 22 suitably secured thereto for connection to operator means for moving the plunger longitudinally within the barrel 12 to effect selective discharge of fluid from the barrel through the discharge end 14.

The discharge end 14 of the syringe cartridge 10 includes a metallic cap 24 which is sealingly affixed to the discharge end of the barrel 12 in a conventional manner. The cap 24 has a peripheral threaded portion 26 to which may be secured a cartridge holder as will become more apparent hereinbelow. The discharge end 14 further includes a needle 27 through which fluid within the barrel 12 may be discharged, with the needle being normally inserted into one's body for intravenous injection of the fluid. A protective cover 28 made of glass, plastic or other suitable material is releasably mounted over the needle 27 to protect it and keep it sanitized during storage preparatory to use. The end of the barrel 12 opposite the discharge end 14 is open to allow insertion of the plunger 18, the open end of the barrel defining an annular end edge surface 30 which serves as a stop surface.

As noted, the syringe cartridge 10 is of known design. One such disposable syringe cartridge of the type as shown in FIG. 1 is commercially available from Wyeth Laboratories, Philadelphia, PA.

The present invention is directed to operator means for use with the syringe cartridge 10 to facilitate handling and manipulation of the syringe cartridge to effect discharge of one or more predetermined dosages from the syringe cartridge. With reference to FIGS. 2–4, one embodiment of operator means in accordance with the present invention is indicated generally at 32. The operator means 32 is cooperable with the plunger 18 to facilitate movement of the plunger relative to the barrel means 12 in a direction to effect discharge of a predetermined quantity of fluid from the syringe cartridge 10. The operator means 32 includes a generally cylindrical actuator shaft 34 and a cylindrical tubular sleeve 36. The tubular sleeve 36 is coaxial with the actuator shaft 34 and defines therewith an annular recess 38. The rearward or right-hand portion of the actuator shaft 34, considered in FIG. 2, may be tubular and is connected to the coaxial sleeve portion 36 through an annular web or wall 40 lying in a plane perpendicular to the longitudinal axis of actuator shaft 34. The wall 40 defines a stop surface 42 which forms the rearward end of the recess 38.

The actuator shaft 34 has an axial threaded bore 44 which is adapted for threaded connection to the threaded connector shaft 22 on the plunger 18. The outer diameter of the actuator shaft 34 and the inner peripheral surface of the sleeve 36 are sized such that the wall of the syringe barrel 12 may be readily received within the annular recess 38 in a manner to allow longitudinal movement of the operator means 32 relative to the syringe barrel 12 in a direction toward the discharge end 14 of the syringe cartridge. The wall 40 of the operator means 32 may be recessed at 46 to provide a thumb-hold recess.

It will be appreciated that with the operator means 32 connected to the plunger 18, movement of the operator means 32 longitudinally along the syringe barrel 12 toward the discharge end 14 will effect movement of the plunger 18 in a direction to discharge fluid from the barrel 12 through the needle 27. As the operator means 32 is moved in a discharge direction, the tubular barrel 12 is progressively received within the recess 38 such that the sleeve 36 progressively telescopingly covers the barrel to protect it from fracture during operation. The sleeve 36 further serves to stabilize the operator means 32 by preventing cocking or other inadvertent misalignment of the operator means with the barrel 12.

The forward end surface 48 on the actuator shaft 34 is spaced a predetermined longitudinal distance from the stop surface 42 of the operator means 32 such that during operation, the operator means 32 may be moved from its initial rearward position, as shown in solid lines in FIG. 2, to a position wherein the stop surface 30 on barrel 12 abuts the stop surface 42, as shown in phantom, to effect a predetermined fluid dosage discharge from the syringe cartridge.

To facilitate manipulation of the syringe cartridge 10 and associated operator means 32 when connected to the plunger 18, cartridge holder means, indicated generally at 50, are preferably provided. The cartridge holder means 50 may be made of a suitable plastic material and includes a generally tubular portion 52 which is adapted to be received over the metallic cap 24 on the syringe cartridge 10. The tubular portion 52 includes an internal threaded axial bore 54 adapted for threaded engagement with the external peripheral threads 26 on the cap 24 of the syringe cartridge so as to releasably retain the holder means 50 on the syringe cartridge. A pair of diametrically opposed radially extending arms 56 and 58 are formed integral with the tubular portion 52 of the cartridge holder means 50 to provide finger holds. In this manner, a syringe cartridge 10 having operator means 32 and holder means 50 secured thereon may be placed in the user's hand with the holder means between two fingers and with the user's thumb engaging the thumb-hold recess 46 to facilitate handling and operating manipulation.

FIG. 5 illustrates another embodiment of operator means, indicated generally at 60, in accordance with the present invention for use with the syringe cartridge 10 to facilitate discharge of two predetermined dosages from the syringe cartridge. The operator means 60 includes a generally cylindrical actuator shaft 62 and an outer cylindrical tubular sleeve portion 64 which is formed coaxial with the actuator shaft portion 62. The tubular sleeve 64 is connected to the actuator shaft 62 through a radial interconnecting wall or web 66 disposed in a plane perpendicular to the axis of the actuator shaft 62. In the embodiment illustrated in FIG. 5, the wall 66 is formed at approximately the mid-length of the sleeve 64. The inner peripheral surface of the sleeve 64 is spaced outwardly from the outer peripheral surface of the actuator shaft 64 to define an annular redess therebetween which is divided by the wall 66 into two axially aligned annular recesses 68 and 70.

The actuator shaft 62 has a threaded bore 44' formed in an end surface 48'. The end surface 48' is spaced longitudinally from an inner stop suface 72 defined by the wall 66 a predetermined distance. The opposite end of the actuator shaft 62 defines a stop surface 74 which is spaced longitudinally from a second stop surface 76 defined by the wall 66 a distance greater than the aforementioned distance between the end surface 48' and the stop surface 72.

The operator means 60 is adapted to be placed in a first cooperative position with a syringe cartridge 10 wherein the threaded bore 44' is connected to the connector shaft 22 of the associated plunger 18. Thereafter, movement of the operator means 60 longitudinally toward the discharge end 14 of the syringe cartridge will effect discharge of fluid from the barrel 12 through the needle 27, the cover 28 having been previously removed from the needle. Such movement of the operator means 60 until the end surface 30 of the barrel 12 abuts the stop surface 72 will effect a first predetermined dosage discharge from the syringe 10. After the first dosage discharge, the operator means 60 may be disconnected from the connector shaft 22 of the plunger 18 and turned end-for-end. The end stop surface 74 on the actuator shaft 62 is then caused to engage the plunger 18, with the connector shaft 22 being received within an axial bore 78 formed in the actuator shaft. With the actuator shaft 62 so positioned, movement of the operator means 60 toward the discharge end 14 of the syringe cartridge 10 until the end 30 of the barrel 12 abuts the stop surface 76 will effect a second predetermined dosage discharge from the needle 27. It will be understood that the distance between the end surface 74 and the stop surface 76 must by necessity be greater than the distance between the end 48' and the stop surface 72. The difference in these distances establishes the second dosage discharge. By proper dimensioning of the distances between the end surfaces 48' and 74 and their associated stop surfaces 72 and 76, respectively, the first and second dosage discharge volumes may be made equal or different, as desired.

It can be seen that as the operator means 60 is moved longitudinally relative to the syringe barrel 12 to effect the first and second dosage discharges, the sleeve 64 progressively telescopes the barrel 12 in a manner to protect the barrel from breakage as well as to stabilize the sleeve on the barrel.

FIGS. 6–10 illustrate another embodiment of the present invention wherein operator means, indicated generally at 80, includes both plunger actuator means, indicated generally at 82, and syringe cartridge holder means, indicated generally at 84. The plunger actuator means 82 and syringe cartridge holder means 84 are cooperable with a syringe cartridge 10 to facilitate discharge of three predetermined dosages from the syringe cartridge.

The plunger actuator means 82 includes a cylindrical actuator shaft portion 86 which has a threaded bore 88 adapted for threaded connection to the connector shaft 22 of a plunger 18 disposed within the barrel portion 12 of a syringe cartridge 10. The plunger actuator means 82 also includes a sleeve portion 90 which is coaxial with the actuator shaft 86 and is spaced therefrom to define an annular recess 92 adapted to receive the wall of the barrel 12 when the actuator means 82 is moved longitudinally toward the discharge end 14 of the syringe cartridge 10 during operation.

The sleeve 90 includes a forward cylindrical tubular portion 90a and a rearward portion 90b which has a substantially square outer peripheral configuration as seen in FIG. 8. The squared rearward portion 90b of the sleeve 90 defines at its intersection with the foward tubular portion 90a first stop shoulder surfaces 94 and 96 which lie in a common plane perpendicular to the longitudinal axis of sleeve 90 and are spaced a predetermined distance from the forward end surface 89 of the actuator shaft 86. The rearward end portion 90b of sleeve 90 defines second stop surfaces 98 and 100 (FIGS. 7 and 8) which lie in a common plane normal to the longitudinal axis of sleeve 90 and are spaced rearwardly from the end surface 89 on the actuator shaft 86 a predetermined distance greater than the longitudinal distance between the planes of surface 89 and the stop surfaces 94 and 96.

The sleeve 90 is connected to the actuator shaft portion 86 through a web or wall 102 which defines a generally annular stop surface 104 at the rearward end of the recess 92. The stop surface 104 is spaced longitudinally rearwardly from the forward surface 89 of the actuator shaft 86 a predetermined distance, which distance is greater than the distances by which the stop surfaces 94, 96 and 98, 100 are spaced from the surface 89. During operation, the stop surface 104 serves to abut the end surface 30 of the syringe cartridge barrel 12 to limit longitudinal movement of the actuator shaft 86, and thus the plunger 18, relative to the syringe barrel 12.

The syringe cartridge holder means 84 includes a forward end portion 108 which has an axial recess 110 and a threaded bore 112 to receive the cap 24 and threaded portion 26 of a syringe cartridge 10 for connection therewith in similar fashion to the above-described cartridge holder means 50. The cartridge holder means 86 includes four equal length longitudinally extending arms 114 which are equidistantly circumferentially spaced about the longitudinal axis of the cartridge holder means 84. Each of the arms 114 has a radially extending leg portion 116 formed integral therewith at the end of the arm opposite the forward end 108. The leg portions 116 define stop surfaces 118 which lie in a common plane normal to the longitudinal axis of the cartridge holder means 84. The plane of the stop surfaces 118 is located at a fixed predetermined position relative to the plane of the stop surface 30 on the syringe barrel 12, and preferably is coplanar therewith when the holder means 86 is mounted on a syringe cartridge.

The cartridge holder means 84 is preferably made of a plastic material, such as natural polypropylene, such that the longitudinally extending arms 114 may be selectively flexed radially inwardly from their normal positions, as shown in solid lines in FIG. 6, to positions disposed against the peripheral surface of the cartridge barrel 12, as shown in phantom in FIG. 6. The arms 114 are normally spaced outwardly from the cartridge barrel 12 in coaxial relation therewith, when the cartridge holder means 84 is assembled onto a syringe cartridge, sufficiently to allow both the forward cylindrical sleeve portion 90a and the rearward squared portion 90b of the sleeve 90 to be received longitudinally within the arms 114.

In operation, the plunger actuator means 82 and cartridge holder means 84 are assembled onto the connector shaft 22 and the forward end cap 24, respectively, of a syringe cartridge 10 as shown in FIG. 6. It will be understood that the syringe barrel 12 initially contains a predetermined quantity, such as 2 cc, of a desired liquid. With the plunger actuator means 82 so connected to the plunger 18, the stop surfaces 94 and 96 on the sleeve 90 are spaced longitudinally from the plane of the stop surfaces 118 on the syringe holder arms 114 a predetermined distance. By pressing the arms 114 against the outer surface of the tubular portion 90a of sleeve 90, movement of the plunger actuator 82 in a forward longitudinal direction until the stop surfaces 94 and 96 engage the stop surfaces 118 on the adjacent inwardly flexed arms 114 will effect a first predetermined dosage discharge from the syringe device 10. Only two of the arms 114, namely, the two aligned with the stop surfaces 94 and 96, need be pressed against the outer surface of the sleeve 90.

After the initial dosage discharge from the syringe device 10, the arms 114 of the cartridge holder 84 which have been pressed against the cylindrical sleeve 90 are released whereafter the plunger actuator 82 may be moved further longitudinally inwardly relative to the cartridge barrel 12. At this time, the two arms 114 disposed at 90° to the two previously inwardly depressed arms 114 are pressed against the sleeve 90 such that the associated stop surfaces 118 thereon will abut the stop surfaces 98 and 100 on the sleeve 90 to limit such further longitudinally inward movement of the plunger actuator 82. Movement of the actuator 82 from its position wherein the stop surfaces 94 and 96 engage the corresponding stop surfaces 118, to the position wherein the stop surfaces 98 and 100 engage the corresponding depressed stop surfaces 118 effects a second predetermined dosage discharge from the syringe cartridge.

A third predetermined dosage discharge from the syringe cartridge 10 is effected by releasing the arms 114 of the plunger holder 84 to allow still further longitudinal movement of the plunger actuator 82 in a discharge direction. Such further movement of the plunger actuator 82 is limited by engagement of the end surface 30 on the cartridge barrel 12 with the stop surface 104 within the recess 92 in the actuator plunger. The distance between the stop surfaces 30 and 104 when the plunger actuator 82 is in its second discharge position, i.e., with stop surfaces 98 and 100 engaging stop surfaces 118 determines the third predetermined dosage discharge from the syringe cartridge 10. By proper dimensioning of the longitudinal distances between the planes of surfaces 89, 94–96, 98–100 and 104, the three discharge dosages may be made equal or different, as desired.

As the tubular sleeve 90 of the plunger actuator 82 is moved longitudinally forwardly relative to the barrel 12 so as to progressively telescope the barrel 12, the sleeve protects the barrel from breakage and assists in stabilizing the plunger actuator on the syringe cartridge.

Having thus described preferred embodiments of the present invention, it can be seen that operator means are provided for use with a syringe cartridge which serve to progressively telescope and protect the syringe barrel from breakage during operation, and which stabilize the plunger actuator during a discharge function. Additionally, the operator means in accordance with the present invention provide for discharge of one or more predetermined dosages from a syringe cartridge.

While preferred embodiments of the present invention have been illustrated and described, it will be understood to those skilled in the art that changes and modifications may be made therein without departing from the invention in its broader aspects. Various features of the invention are set forth in the following claims.

What is claimed is:

1. A syringe device comprising, in combination, barrel means defining an internal chamber adapted to contain a quantity of fluid, discharge means mounted on one end of said barrel means through which said fluid may be discharged, plunger means disposed within said chamber and movable to effect discharge of said fluid, and operator means cooperable with said plunger means and operable to move said plunger means to effect said discharge of fluid, said operator means including a sleeve portion adapted to receive said barrel means therein and progressively telescope said barrel means as said operator means is moved longitudinally relative to said barrel means to effect fluid discharge from said discharge means, said operator means including first stop means adapted for engagement with said barrel means to limit movement of said operator means in a discharge direction relative to said barrel means whereby to establish a first predetermined dosage discharge from said syringe, said operator means being reversible end-for-end and longitudinally movable relative to said barrel means in a reversed position to move said plunger means in a discharge direction, said operator means including second stop means operable to engage said barrel means and limit longitudinal movement of said operator means in a discharge direction relative to said barrel means when said operator means is in its reversed position, whereby to effect a second predetermined dosage discharge from said syringe.

2. A syringe device as claimed in claim 1 including finger grip means mounted on said barrel means generally adjacent the end thereof on which said discharge means is mounted, said finger grip means including a pair of diametrically opposed projections for grasping by one's fingers to assist in movement of said operator means relative to said barrel means while the syringe is held in one's hand.

3. A syringe device as defined in claim 1 wherein said plunger has an externally threaded connector shaft extending therefrom opposite said fluid, said actuator shaft having an internally threaded bore adapted for threaded connection to said threaded connector shaft so as to effect a positive connection between said actuator shaft and said plunger.

4. A syringe device comprising, in combination, generally tubular barrel means defining an internal chamber adapted to contain a quantity of fluid and having a stop surface thereon, discharge means mounted on one end of said barrel means through which said fluid may be discharged, plunger means disposed within said chamber and movable to effect discharge of said fluid, and operator means cooperable with said plunger means and operable to move said plunger means to effect said discharge of fluid, said operator means including an operator shaft having first and second end portions adapted for engagement with said plunger means to move said plunger means in a direction to discharge fluid from said chamber, said operator means further including a generally tubular sleeve portion disposed in coaxial relation with said operator shaft to define an annular recess therebetween to receive said barrel means therein as said operator means is moved to effect discharge from the syringe, and including a stop element disposed within said recess and positioned to engage said stop surface on said barrel means and limit fluid discharge to a first predetermined dosage when said operator means is moved in a discharge direction with said first end portion of said operator shaft engaging said plunger means, said stop element being adapted for engagement with said stop surface to limit discharge to a second predetermined dosage when said operator means is moved in a discharge direction with said second end portion of said operator shaft engaging said plunger means.

5. Operator means for use with a syringe cartridge which includes a rigid walled tubular syringe barrel adapted to contain a quantity of fluid, said cartridge having discharge means on one end of said barrel and including plunger means disposed within said barrel and movable to effect discharge of fluid from said barrel through said discharge means, said syringe barrel defining a rigid barrel stop surface on the end thereof opposite said discharge means, said operator means including an actuator shaft having a first end cooperable with said plunger means to effect movement of said plunger means in a direction to discharge fluid from said chamber, said operator means further having a sleeve generally coaxial with said shaft and being spaced therefrom to define a recess to receive said barrel longitudinally therein such that movement of said operator means relative to said barrel in a direction to cause discharge from said barrel causes said sleeve to progressively telescope said barrel and protect said barrel from fracture, said actuator shaft and sleeve defining a first stop surface therebetween engageable with said barrel stop surface to limit movement of said operator means relative to said barrel in a first discharge direction so as to establish a first discharge from said barrel, said operator means being reversible end-for-end relative to said barrel and defining a second end surface on said actuator shaft adapted for cooperation with said plunger means to move said plunger means in a direction to effect discharge from said barrel, said actuator shaft and said sleeve defining a second stop surface therebetween adapted for engagement with said barrel stop surface to establish a second discharge from said barrel.

* * * * *